US010092670B2

(12) United States Patent
Mason

(10) Patent No.: US 10,092,670 B2
(45) Date of Patent: Oct. 9, 2018

(54) MEDICAL ACCESSORY HOLDER

(71) Applicant: Medicart International Limited, Shoeburyness (GB)

(72) Inventor: David Robert Mason, Shoeburyness (GB)

(73) Assignee: Cantel (UK) Limited, Southend-on-Sea, Essex (GB)

( * ) Notice: Subject to any disclaimer, the term of this patent is extended or adjusted under 35 U.S.C. 154(b) by 263 days.

(21) Appl. No.: 14/888,322

(22) PCT Filed: Apr. 16, 2014

(86) PCT No.: PCT/GB2014/051191
§ 371 (c)(1),
(2) Date: Oct. 30, 2015

(87) PCT Pub. No.: WO2014/177838
PCT Pub. Date: Nov. 6, 2014

(65) Prior Publication Data
US 2016/0058518 A1 Mar. 3, 2016

(30) Foreign Application Priority Data
May 2, 2013 (GB) .................................. 1307983.5

(51) Int. Cl.
*A61L 2/26* (2006.01)
*A61L 2/18* (2006.01)
(Continued)

(52) U.S. Cl.
CPC ................ *A61L 2/26* (2013.01); *A61B 19/26* (2013.01); *A61B 50/20* (2016.02); *A61B 50/33* (2016.02);
(Continued)

(58) Field of Classification Search
CPC .................................. A61L 2/26; A61B 50/20
See application file for complete search history.

(56) References Cited

U.S. PATENT DOCUMENTS 3,013,656 A 12/1961 Murphy, Jr.
4,607,868 A * 8/1986 Harvey ................ A61M 39/10
285/12

(Continued)

FOREIGN PATENT DOCUMENTS

DE 202005015801 U1 12/2005
GB 2485011 A 5/2012
GB 2485818 A 5/2012

OTHER PUBLICATIONS

International Search Report dated Aug. 18, 2014 of the International Searching Authority, European Patent Office, of International Patent Application No. PCT/GB2014/051191 filed Apr. 16, 2014.

*Primary Examiner* — Donald R Spamer
(74) *Attorney, Agent, or Firm* — Sorell, Lenna & Schmidt, LLP; William D. Schmidt, Esq.

(57) ABSTRACT

A medical accessory holder (10) is provided for use during processing of medical equipment. The holder (10) comprises a tray portion (11), retaining means (16, 17) associated with the tray portion (11), and securing means (13) provided on the tray portion (11). The retaining means (16, 17) are adapted to engage with a medical accessory (20) such that, once engaged, the medical accessory (20) cannot be disengaged without breaking the medical accessory holder (10), thereby rendering the holder (10) suitable only for single use. The securing means (13) enable the holder (10) to be secured to an article of medical equipment with which the medical accessory (20) is associated, during processing thereof.

10 Claims, 2 Drawing Sheets

(51) Int. Cl.
*A61L 2/24* (2006.01)
*A61B 19/00* (2006.01)
*B65D 1/34* (2006.01)
*A61B 90/70* (2016.01)
*A61B 50/20* (2016.01)
*A61B 50/33* (2016.01)
*A61B 50/30* (2016.01)
*A61B 90/00* (2016.01)

(52) U.S. Cl.
CPC .............. *A61B 90/70* (2016.02); *A61L 2/186* (2013.01); *A61L 2/24* (2013.01); *B65D 1/34* (2013.01); *A61B 50/30* (2016.02); *A61B 2090/0814* (2016.02); *A61B 2090/701* (2016.02); *A61L 2202/24* (2013.01)

(56) References Cited

U.S. PATENT DOCUMENTS

| | | |
|---|---|---|
| 4,711,352 A | 12/1987 | Williams et al. |
| 5,993,754 A | 11/1999 | Lemmon et al. |
| 2013/0220855 A1* | 8/2013 | Markovitch .............. A61L 2/26 206/363 |

* cited by examiner

MEDICAL ACCESSORY HOLDER

This invention relates to a medical accessory holder for use in processing and conditioning. In particular, it relates to a single-use holder for retaining the valves of a flexible medical endoscope during processing and conditioning. The term "processing" is used herein to refer to cleaning and high level disinfection of medical equipment following its use on a patient. The term "conditioning" is used herein to herein to refer to maintaining the disinfection of medical equipment following processing thereof to a state of high level disinfection.

Following use on a patient, medical equipment must be processed to, and maintained at, a high level of disinfection. This is a particular necessity for medical equipment utilised in invasive procedures, such as flexible medical endoscopes, with which the present invention is primarily concerned.

Flexible medical endoscopes typically comprise a number of auxiliary channels for the delivery of air, water or other fluids. These may be utilised for the delivery of such fluids to the interior of a patient where this is required during a medical procedure, for the removal of fluid (by suction) from the interior of patient, or for cleaning the viewing window or lens of the endoscope. Operation of these channels is typically controlled by a number of valves (sometimes referred to as pistons) operated remotely by the practitioner carrying out the endoscopy procedure.

During processing of the flexible medical endoscope following its use on a patient, the valves must be removed, in order that each of the auxiliary channels can be thoroughly cleaned and disinfected. The valves themselves must also be subjected to the same processing regime to bring them to a state of high level disinfection. Typically, processing of flexible medical endoscopes and associated accessories such as the valves, is now carried out on an automated basis using a specially designed processing machine, known as an Automated Endoscope Reprocessing (AER) machine or an Endoscope Washer and Disinfector (EWD). In a busy hospital endoscopy department this can cause problems, since the valves specific to a particular endoscope can easily become separated from that endoscope during processing. This can lead to cross-contamination if a set of valves associated with one endoscope are accidentally inserted into a different endoscope.

Accessories such as endoscope valves are often placed into auxiliary containers, before being placed into the AER machine along with the endoscope. Ideally, such auxiliary containers should only be used once, and then disposed of, in order to eliminate them as a possible source of cross-contamination between different endoscopes which may be processed using the same machine. Indeed, concerns regarding the levels of disinfection to which endoscopes and their associated accessories are processed, and at which they are maintained, have led to increasingly strict guidelines regulating the manner in which processing is carried out. For example, the British Society of Gastroenterology (BSG) Guidelines for Decontamination of Equipment for Gastrointestinal Endoscopy stipulate that such auxiliary containers must be single use items, and must be disposed of after use. In practice however, this ideal is not always achieved, in particular since it is often not possible to tell whether a container has been used previously.

The Applicant's own UK Patent Publication No. GB 2,485,818 discloses a container for housing a medical accessory during processing. The container has a closure mechanism adapted such that once closed it cannot be re-opened without the container breaking. The container is thus rendered suitable only for single use.

The Applicant's own UK Patent Publication No. GB 2,483,741 discloses a method and apparatus, referred to as a conditioning station, for conditioning a flexible medical endoscope by delivering disinfectant fluid to the internal channels of the endoscope.

The present invention seeks to improve upon the device of GB 2,485,818, by providing a single use medical accessory holder for retaining the valves of a flexible medical endoscope during both processing and conditioning, and which is adapted for use with the method and apparatus of GB 2,482,741. Although the medical accessory holder of the present invention has been developed with endoscope valves in mind, it is envisaged that the holder may be adapted for use with substantially all kinds of medical accessory, and the disclosure of the invention herein should be construed accordingly.

According to the present invention there is provided a medical accessory holder for use during processing of medical equipment, said holder comprising:

a tray portion;

retaining means associated with the tray portion and adapted to engage with a medical accessory such that, once engaged, said medical accessory cannot be disengaged without breaking the medical accessory holder, thereby rendering said holder suitable only for single use; and securing means provided on the tray portion to enable said holder to be secured to an article of medical equipment with which said medical accessory is associated, during processing thereof.

The medical accessory holder of the present invention is intended for use during processing and conditioning of medical equipment. In particular, it is adapted to be processed in a medical equipment processing machine—such as an automated endoscope reprocessing (AER/EWD) machine in the preferred case where the medical accessory is a component of a flexible medical endoscope. To that end, the tray portion preferably has perforations to permit the flow of water or other cleaning fluids therethrough.

The securing means is preferably adapted to enable said holder to be secured to a flexible medical endoscope—and in particular, the specific flexible medical endoscope with which the component is associated—during processing thereof. The securing means may conveniently be or comprise a clip element, such as a flexible plastics omega-shaped clip element.

The flexible medical endoscope component for which the medical accessory holder of the present invention has been particularly developed are the valves associated with the endoscope's auxiliary air, water and suction channels. The holder is preferably adapted to hold two or more flexible medical endoscope valves, and most preferably is adapted to hold all valves associated with a specific endoscope. To this end, the holder preferably comprises two or more retaining means, each adapted to hold a flexible medical endoscope valve. The or each retaining means is preferably adapted to hold a flexible medical endoscope valve in an orientation aligned with the plane of the tray portion.

As hereinbefore described, the retaining means is adapted to engage with a medical accessory—for example, an endoscope valve—such that, once engaged, the medical accessory cannot be disengaged without breaking the holder, thereby rendering the holder suitable only for single use. Preferably, the retaining means is adapted such that, once engaged, said medical accessory cannot be disengaged without breaking the retaining means. This may be achieved by forming the or each retaining means with a weakened section adapted to be easily broken in order to retrieve said medical accessory.

In one embodiment of the present invention, the or each retaining means upstand from the tray portion. This embodiment preferably further comprises a backstop element upstanding from the tray portion, such that in use a medical accessory held by the or each upstanding retaining means may abut against said backstop element, in order to be held more securely.

The or each upstanding retaining means preferably is or comprises a clip element—and this may conveniently be a flexible plastics omega-shaped clip element (of similar construction to that of the securing means) to enable engagement with a flexible medical endoscope valve. The or each clip element is preferably adapted to be easily broken in order to retrieve said medical accessory.

In an alternative embodiment of the present invention, the or each retaining means is or comprises a recess formed in the tray portion, each said recess being adapted to receive a medical accessory, such as a flexible medical endoscope valve.

In this embodiment the retaining means preferably further comprises a retaining bar adapted to extend over each recess, thereby to retain each said medical accessory therein. The retaining bar is preferably adapted to be easily broken in order to retrieve said medical accessory. Most preferably, the retaining bar is connected to the tray portion via a live hinge, said hinge being adapted to be easily broken in order to retrieve said medical accessory.

The retaining bar may optionally also be provided, at its end distal from said hinge, with a socket adapted to engage with a peg upstanding from said tray portion, such that once engaged, said peg cannot be disengaged from said socket without breaking the retaining bar, or some other part of the holder.

In either embodiment, the holder may preferably further comprise a connector adapted to deliver fluid to a held medical accessory. This adaptation enables the medical accessory holder to be utilised in combination with a conditioning station. The connector is preferably formed with a luer taper to enable connection to a conditioning station, such as that described in the Applicant's GB 2,483,741.

The holder may preferably further comprise an end portion, extending from one end of the tray portion, said end portion housing the connector. Where the medical accessory is a flexible medical endoscope valve, the connector is preferably adapted to deliver cleaning and/or disinfecting fluid, such as dilute aqueous hydrogen peroxide solution, to internal channels of said valve. To this end, the connector is preferably a manifold connector, enabling delivery of different fluids as required.

In a further adaptation of the present invention the holder may further comprise one or more conduits to enable delivery of fluid from the connector to a said medical accessory. In the alternative embodiment described above, in which the retaining means comprise recesses in the tray portion, these conduits may conveniently also be formed within the end portion, extending between the connector and the recesses.

In order that the present invention may be more clearly understood, preferred embodiments thereof will now be described in detail, though only by way of example, with reference to the accompanying drawings, in which.

Figure 1:
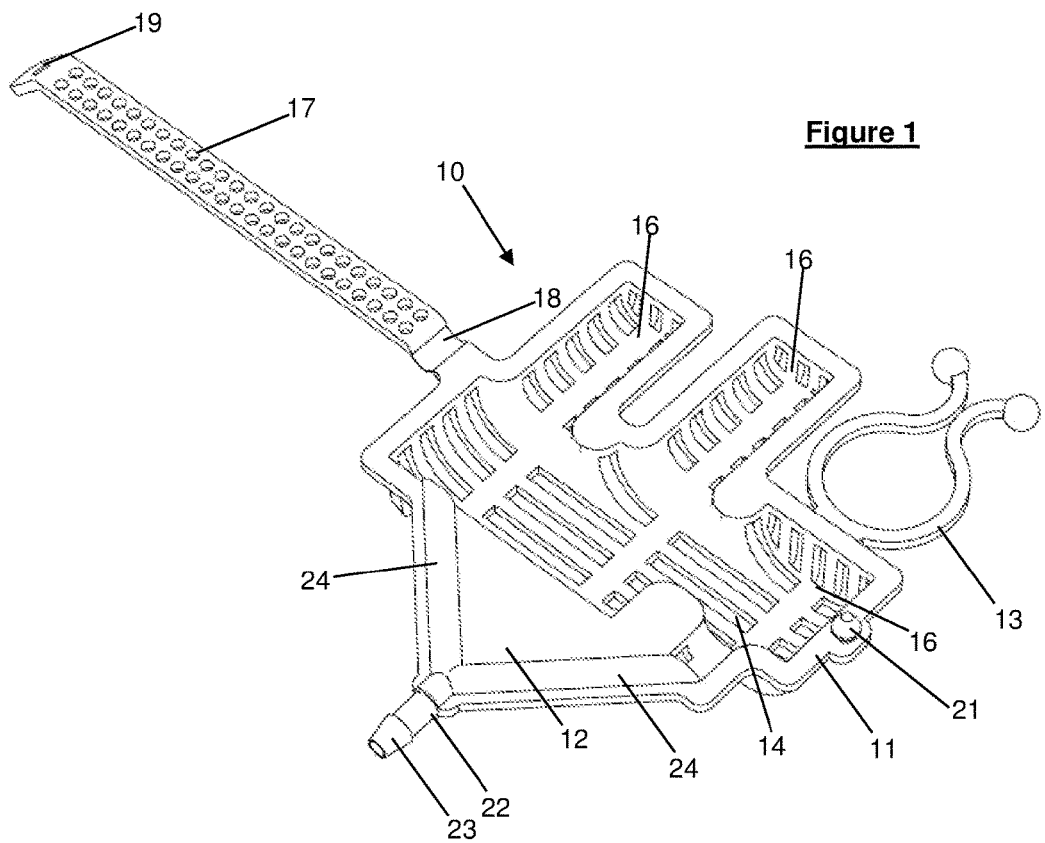
FIG. 1 shows a top view of a medical accessory holder according to a preferred embodiment of the present invention, in an open configuration.
Figure 2:
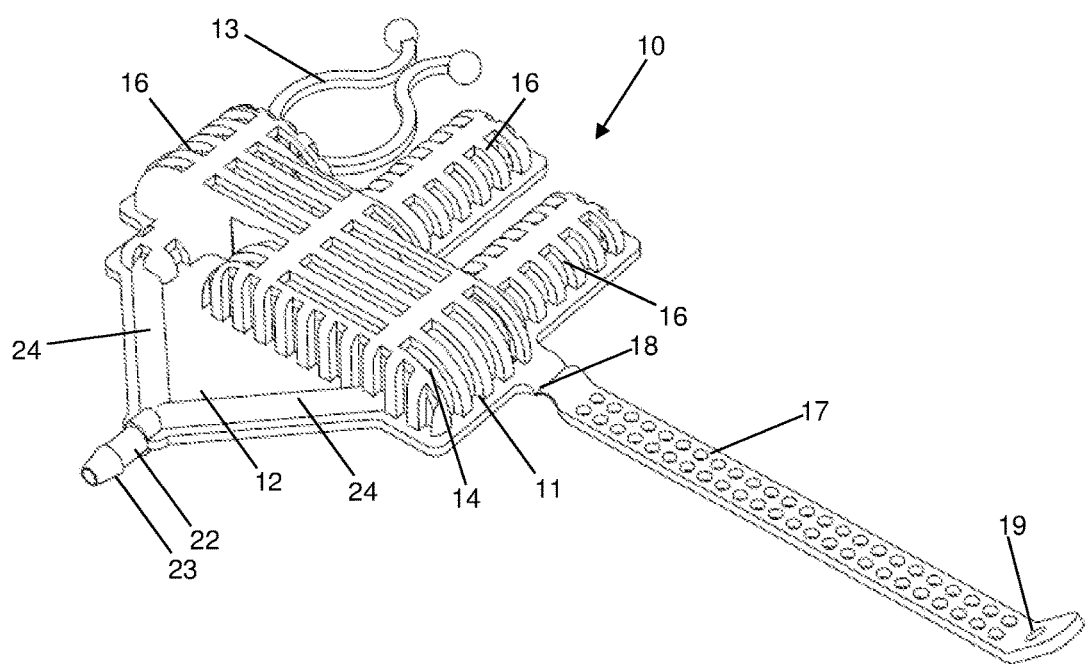
FIG. 2 shows an underside view of the medical accessory holder of FIG. 1.

Referring first to FIGS. 1 and 2, there is shown a medical accessory holder, generally indicated 10, according to a preferred embodiment of the present invention. The holder 10 comprises a tray portion 11 with an end portion 12 extending therefrom. The tray portion 11 is provided with securing means, in the form of a flexible plastic clip element 13, which in use serves to attach the holder 10 to a flexible medical endoscope during processing thereof.

As can be seen, the tray portion 11 is provided with multiple perforations 14, so as to allow the flow of water and other cleaning or disinfecting fluids therethrough during processing and conditioning.

The medical accessory holder 10 is provided with recesses 16 moulded in the body of the tray portion 11, each shaped so as to receive a flexible medical endoscope valve (not shown in FIGS. 1 and 2). As can be seen from FIG. 1, each recess 16 may be shaped so as to accommodate a specific size and shape of endoscope valve. A retaining bar 17 is provided on the tray portion 11, connected thereto via a live hinge 18. At its end distal from the hinge 18, the retaining bar 17 is provided with a socket 19 adapted to engage with an upstanding peg 21 formed on the tray portion 11. Together, the recesses 16 and the retaining bar 17 constitute the retaining means of the preferred embodiment of accessory holder 10.

It is important that the holder 10 operates as a single use device and, as will be described in more detail below with reference to FIGS. 3 and 4, to this end the retaining means is adapted such that flexible medical endoscope valves housed within the holder 10 cannot be retrieved therefrom without breaking the retaining means, thus rendering the holder 10 for further use. This is achieved by constructing the retaining bar 17 with a weakened section, which may most conveniently be formed at the live hinge 18. Alternatively, or additionally, the peg 21 and socket 19 assembly may be formed such that the peg 21 cannot be removed from the socket 19 without breaking one or other of these components.

A manifold connector 22 is provided on the end portion 12 and has a luer taper 23 to facilitate connection to an endoscope conditioning station, such as that described in the applicant's GB 2,483,741. Conduits 24 are formed in the body of the end portion 12, adapted to deliver air, water and cleaning fluids from the manifold connector 22 to the recesses 16.

Figure 3:
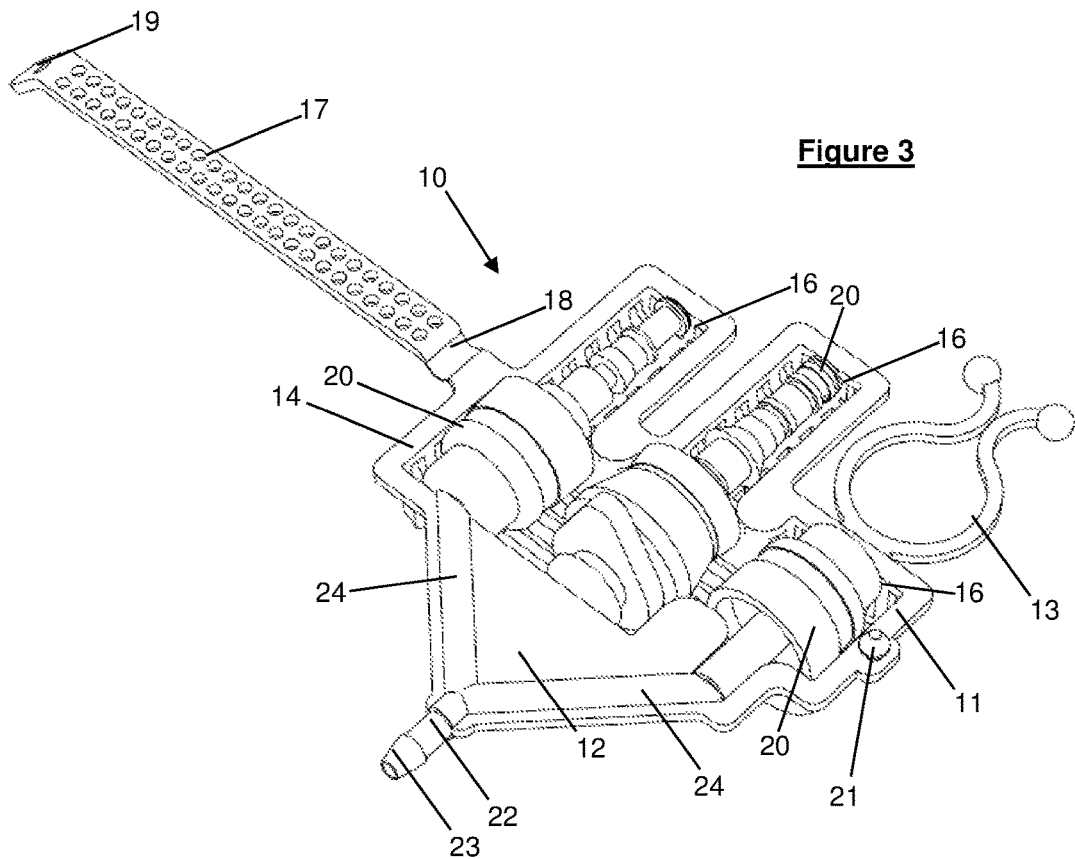
FIG. 3 shows the medical accessory holder of FIGS. 1 and 2, with flexible medical endoscope valves placed therein.
Figure 4:
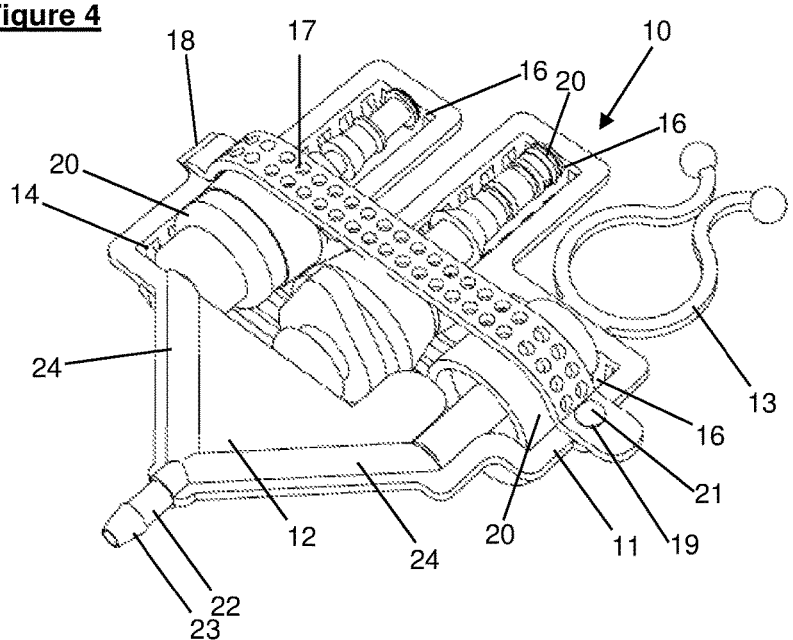
FIG. 4 shows the medical accessory holder and flexible medical endoscope valves of FIG. 3, with the holder in a closed configuration.

Referring now to FIGS. 3 and 4, there is shown the accessory holder 10 in use, holding a set of flexible medical endoscope valves 20 during processing and conditioning. Each valve 20 is accommodated within a recess 16 in the tray portion 11 of the holder 10. Each recess 16 is individually formed so as to accommodate a specific size and shape of endoscope valve 20. In this way, all valves 20 of a particular endoscope can be accommodated. By varying the number, size and shape of the recesses 16, the holder 10 may be produced on a bespoke basis for use with a particular model of endoscope.

Each recess 16 is serviced by a conduit 24 formed within the end portion 12 of the holder 10. Each conduit 24 then connects with the internal channels of the valves 20, when the valves 20 are located in the recesses 16.

Once the valves 20 are in place in the recesses 16 as shown in FIG. 3, the retaining bar 17 is then brought into position by rotating it about its hinge 18, and engaging the pin 21 with the socket 19. The holder 10 is now in its closed configuration as shown in FIG. 4. The retaining bar 17 now secures the valves 20 in place in the recesses 16.

The holder 10 is then attached to the particular endoscope (not shown) with which the valves 20 are associated, by means of the clip element 13. The endoscope and accessory holder 10, with valves 20 therein, are then processed (cleaned) in an AER machine. Following processing, the endoscope and accessory holder 10, with valves 20 still therein, are removed from the AER and placed in an endoscope conditioning station (not shown) as described in the applicant's GB 2,483,741. The connector 22 is then connected to the conditioning station's fluid reservoir, to enable the internal channels of the valves 20 to be charged, via the conduits 24, with air, water and dilute aqueous hydrogen peroxide solution, according to the conditioning station's pre-programmed conditioning sequence.

In order to retrieve the valves 20 from the holder 10 following conditioning, it is necessary to remove the retaining bar 17 from the tray portion 11. However, this can only be done by breaking a portion of the retaining bar 17, which may conveniently be either the hinge 18 or the peg 21 and/or socket 19. This ensures that the accessory holder 10 cannot be used again, and so is then disposed of as a single-use item.

The invention claimed is:

1. A medical accessory holder for use during processing and conditioning of a flexible medical endoscope, said holder comprising:
    a tray portion, having perforations to permit the flow of water or other cleaning fluids therethrough;
    two or more retaining members associated with the tray portion and each adapted to engage with and hold a flexible medical endoscope valve such that, once engaged, each valve cannot be disengaged without breaking the holder, thereby rendering said holder suitable only for single use; wherein each of said retaining members comprise a recess formed in the tray portion, each recess being adapted to receive one of the flexible medical endoscope valves; and
    a retaining bar connected to the tray portion via a hinge, said retaining bar being adapted to extend over each recess to retain each of said valves therein.

2. A medical accessory holder as claimed in claim 1, wherein said holder is adapted to be processed in an automated endoscope reprocessing (AER) machine.

3. A medical accessory holder as claimed in claim 1, wherein the holder further comprises a clip on the tray portion to enable said holder to be secured to a flexible medical endoscope.

4. A medical accessory holder as claimed in claim 1, wherein each of the retaining members is adapted to hold one of the flexible medical endoscope valves in an orientation aligned with the plane of the tray portion.

5. A medical accessory holder as claimed in claim 1, wherein each of the retaining members upstands from the tray portion, the tray portion partially enclosing the flexible medical endoscope valves.

6. A medical accessory holder as claimed in claim 1, wherein the retaining bar is provided, at its end distal from said hinge, with a socket adapted to engage with a peg upstanding from said tray portion, such that once engaged, said peg cannot be disengaged from said socket without breaking said holder.

7. A medical accessory holder as claimed in claim 1, further comprising an end portion extending from one end of the tray portion, said end portion housing a manifold connector and one or more conduits adapted to deliver cleaning and/or disinfecting fluid from a conditioning station to internal channels of each flexible medical endoscope valve.

8. A medical accessory holder as claimed in claim 7, wherein the connector is formed with a luer taper to enable connection to said conditioning station.

9. A medical accessory holder as claimed in claim 7, wherein the connector is adapted to deliver dilute aqueous hydrogen peroxide solution to each flexible medical endoscope valve.

10. A medical accessory holder as claimed in claim 1, wherein when the retaining bar is connected to the tray portion, the retaining bar, the hinge, the holder, or a combination thereof, is adapted to be broken in order to retrieve said valves.

* * * * *